US007607430B2

(12) United States Patent
Davis

(10) Patent No.: US 7,607,430 B2
(45) Date of Patent: Oct. 27, 2009

(54) MAGNETICALLY COUPLED HUMIDIFIER CONTAINER COMPONENTS

(75) Inventor: Mitchell G. Davis, Largo, FL (US)

(73) Assignee: Hana Consulting, Inc., Redington Beach, FL (US)

( * ) Notice: Subject to any disclaimer, the term of this patent is extended or adjusted under 35 U.S.C. 154(b) by 218 days.

(21) Appl. No.: 11/736,664

(22) Filed: Apr. 18, 2007

(65) Prior Publication Data

US 2008/0258854 A1 Oct. 23, 2008

(51) Int. Cl.
*A61M 15/00* (2006.01)
*B65D 51/00* (2006.01)

(52) U.S. Cl. .................. 128/200.11; 335/285; 335/306; 220/230

(58) Field of Classification Search ................. 335/285, 335/306; 128/200.11–200.13; 220/230
See application file for complete search history.

(56) References Cited

U.S. PATENT DOCUMENTS 712,447 A 10/1902 Woolley
2,672,257 A 3/1954 Simmonds
3,961,721 A 6/1976 Gordon et al.
4,010,736 A * 3/1977 Sacomani et al. ........... 126/369
4,301,094 A * 11/1981 Baus ........................... 261/29
4,570,810 A 2/1986 Hawkins
4,747,744 A 5/1988 Dominique et al.
4,854,110 A 8/1989 Korcz
4,991,270 A 2/1991 Aoki
5,131,070 A 7/1992 Chiu et al.
5,405,037 A 4/1995 Piron
5,473,799 A 12/1995 Aoki
5,707,091 A 1/1998 Morita
5,865,482 A 2/1999 Aoki
5,983,464 A 11/1999 Bauer
5,987,715 A 11/1999 Khon
6,131,247 A 10/2000 Morita
6,215,381 B1 4/2001 Aoki
6,295,702 B1 10/2001 Bauer
6,564,434 B1 5/2003 Morita
6,978,521 B2 12/2005 Morita
7,156,252 B2 1/2007 Morin
7,172,101 B2 2/2007 Find
7,178,207 B2 2/2007 Wong et al.
2006/0266359 A1 * 11/2006 Van Beurden et al. .. 128/205.24

OTHER PUBLICATIONS

International Search Report, PCT/US08/59611, dated Jul. 24, 2008.
Written Opinon of the International Searching Authority, PCT/US08/59611, dated Jul. 24, 2008.

* cited by examiner

*Primary Examiner*—Ramon M Barrera
(74) *Attorney, Agent, or Firm*—Vedder Price P.C.

(57) ABSTRACT

A method of coupling the upper and lower section of a humidifier container used to humidify oxygen gas, using magnetic coupling means. A series of corresponding magnets around the container, located externally to the device or internally, secure the lower part or vessel to the upper part or cap. Using magnets opposing an attracted metal may he used in lieu of corresponding magnet to magnet attraction which requires the poles of the magnets be oriented with their poles to attract each other.

29 Claims, 18 Drawing Sheets

MAGNETICALLY COUPLED HUMIDIFIER CONTAINER COMPONENTS

FIELD OF THE INVENTION

The invention relates to a humidifier container used to humidify gasses, such as oxygen and more particularly, to the method of coupling the upper and lower components of the container.

BACKGROUND OF THE INVENTION

The invention herein is directed at a humidifier container used to humidify gasses, most commonly oxygen. The container most commonly holds distilled water in order to humidify the incoming gas when dispensed. It is common practice for medication and other fluids to be mixed as a fluid to humidify the dispensed gas as well.

The invention is directed to the manner in which the lower part of the device, which holds the fluid, is attached to the upper part which receives the dry gas and dispenses the humidified gas.

Currently all devices manufactured for this purpose, utilize a threaded upper section (cap) and a lower section (container vessel or cup). The lower section is turned and tightened with threaded sections to seal the lower section (container vessel or cup) to the upper part of the device.

SUMMARY OF THE INVENTION

The present invention is directed at the manner of coupling the upper and lower section of a humidifier container using magnetic coupling means. A series of corresponding magnets around the perimeter of the device secure the lower part to the upper part. Using magnets opposing an attracted metal may be used as well in place of corresponding magnet to magnet attraction which requires the poles of the magnets be oriented with their poles to attract each other.

This method removes the necessity for a threaded section on either of the parts. The magnetic sections around the perimeter can be placed either inside, along the sealing edge section or on the outside of the device. Locating the magnets on the outside of the device allows ease of alignment visually.

This has three basic benefits:

1) Ease of mating the lower part to the upper part with minimal force or precise threading/mating.

2) Ease of removal. The current method (threading) may be over tightened leading to difficulty in disassembling the device.

3) Eliminates the need for a pressure relief valve currently used on threaded type devices. Should a blockage of the dispensed gas flow exist, current devices have a pressure relief valve fitted on the device to relieve the excess pressure. Using magnetic force to couple the parts of the device has the advantage of the pressure breaking the seal and relieving the excess pressure without the need for the relief valve. The excess pressure overcomes the magnetic coupling force and the excess pressure is vented at the seal. Once the blockage is removed and the gas is allowed to flow freely from the device, the magnetically sealed device reseats itself and normal operation resumes.

The "magnetic fastener" or fastening means can be configured with a single upper and lower fastener in the form of a ring or by magnetizing one part and having the other manufactured from a metal. However, using multiple points allows for easier disassembly by turning one part of the device so that the magnetic fasteners no longer line up with each other and the magnetic force is broken. Given the typical sizes of the devices, it was found that four or more magnet points seem to work the best. Preferably, six "magnetic fastener" points should be positioned equally at 60 degrees points on center. This is useful since the sections can he aligned without regard to a "front" or "back". If needed alignment could be necessitated by orienting the "magnetic fasteners" in such a way that misalignment would be impossible.

In addition, the "magnetic fasteners" can be varied by size. The size of the magnetic mating surfaces will vary dependent upon the size, weight and volume of the humidifier device. It will also vary in size if magnet pairs are used versus magnet against corresponding attracted metal sections.

Shape is also a consideration. The magnetic attractors can vary in shape to conform to the device to maximize magnetic force or adapt to conform to various shapes of the device.

There are three main types of magnets:

a) Permanent magnets: These are permanent in the sense that once they are magnetized, they retain a level of magnetism. Different types of permanent magnets have different characteristics or properties concerning how easily they can be demagnetized, how strong they can be, how their strength varies with temperature, and so on. There are four classes of permanent magnets; a) Neodymium Iron Boron (NdFeB or NIB), b) Samarium Cobalt (SmCo), c) Alnico, and d) Ceramic or Ferrite.

Permanent magnets can be manufactured in almost any shape. Round bars, rectangular bars, disks, rectangles, multi-fingered rings etc., or just about any custom shapes needed. Some are cast into a mold and require grinding to achieve final dimensions. Others start as a powder which is pressed into a mold or pressure bonded or sintered.

Temporary magnets are those which act like a permanent magnet when they are within a strong magnetic field, but lose their magnetism when the magnetic field disappears. Examples would be paperclips, nails, and pieces of iron. These may be used in conjunction with a permanent magnet as one of the components of the "magnetic fastener".

Electromagnets: An electromagnet is a tightly wound helical coil of wire, usually with an iron core, which acts like a permanent magnet when current is flowing in the wire. The strength and polarity of the magnetic field created by the electromagnet are adjustable by changing the magnitude of the current flowing through the wire and by changing the direction of the current flow. This could be utilized but would require an external source for power.

Magnet polarity are typically Bi-polar or Unidirectional.

Magnets strength is rated in value of Gauss. The gauss of the magnet can be changed to suit the application. Permanent ceramic magnets were used in one of the prototypes, rare earth magnets in another. Rare earth magnets are much stronger by weight and volume than ceramic magnets but are more expensive. Typically a rare earth magnet would be smaller and exhibit the same gauss rating of a corresponding larger ceramic magnet.

Rare earth magnets have negative oxidation and temperature concerns.

A permanent magnet will retain its magnetism unless it is affected by a strong outside magnetic or electrical force, or elevated temperatures. If they are not exposed to any of these conditions, permanent magnets will lose magnetism on their own, however this degradation is very slow, on the order of one percentage point every ten years.

DETAILED DESCRIPTION OF THE INVENTION

Figure 1A:
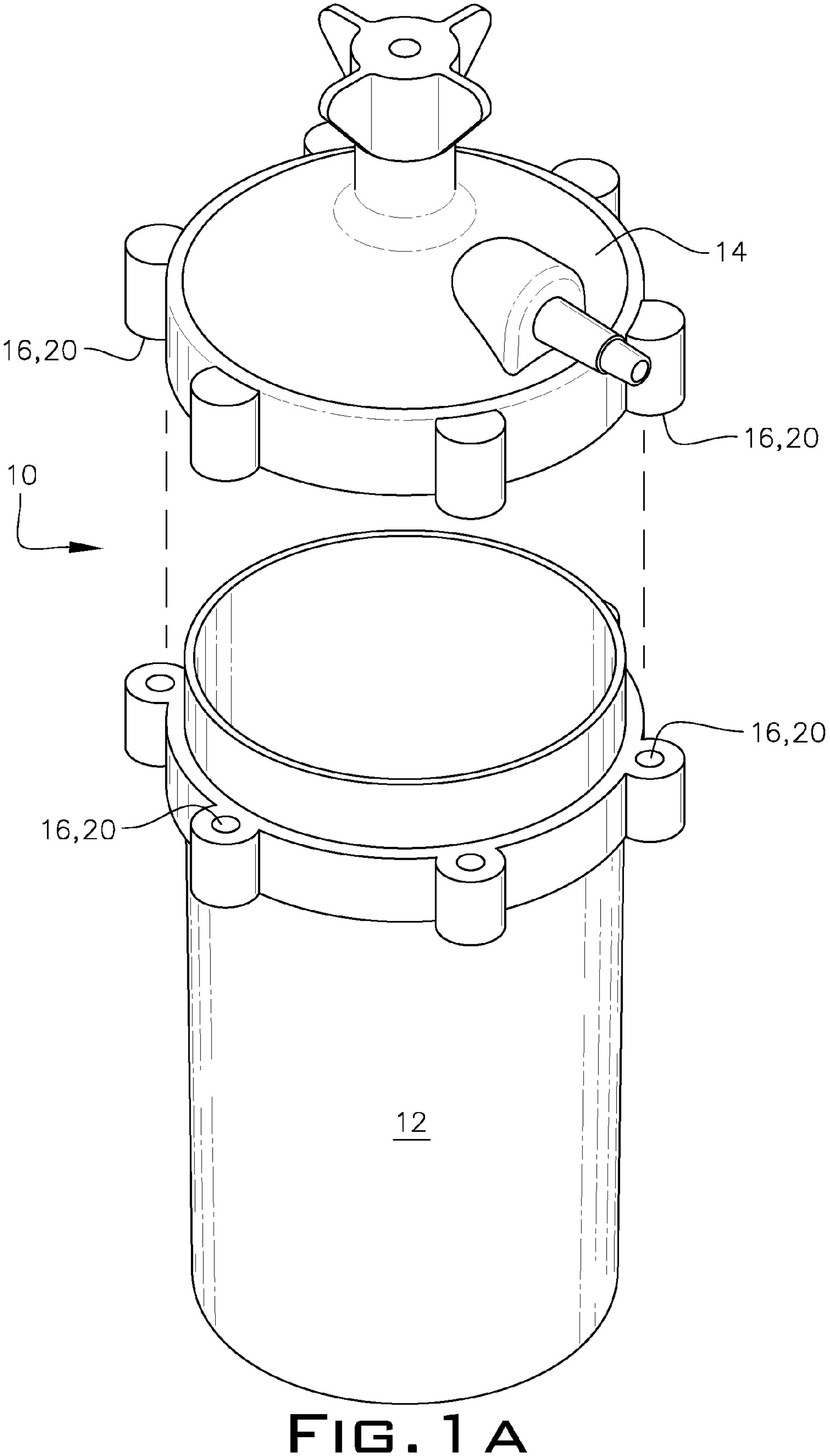
FIG. 1A is a perspective exploded view of one embodiment of the present invention depicting external generally round magnets for the coupling of the upper and lower sections.
Figure 1B:
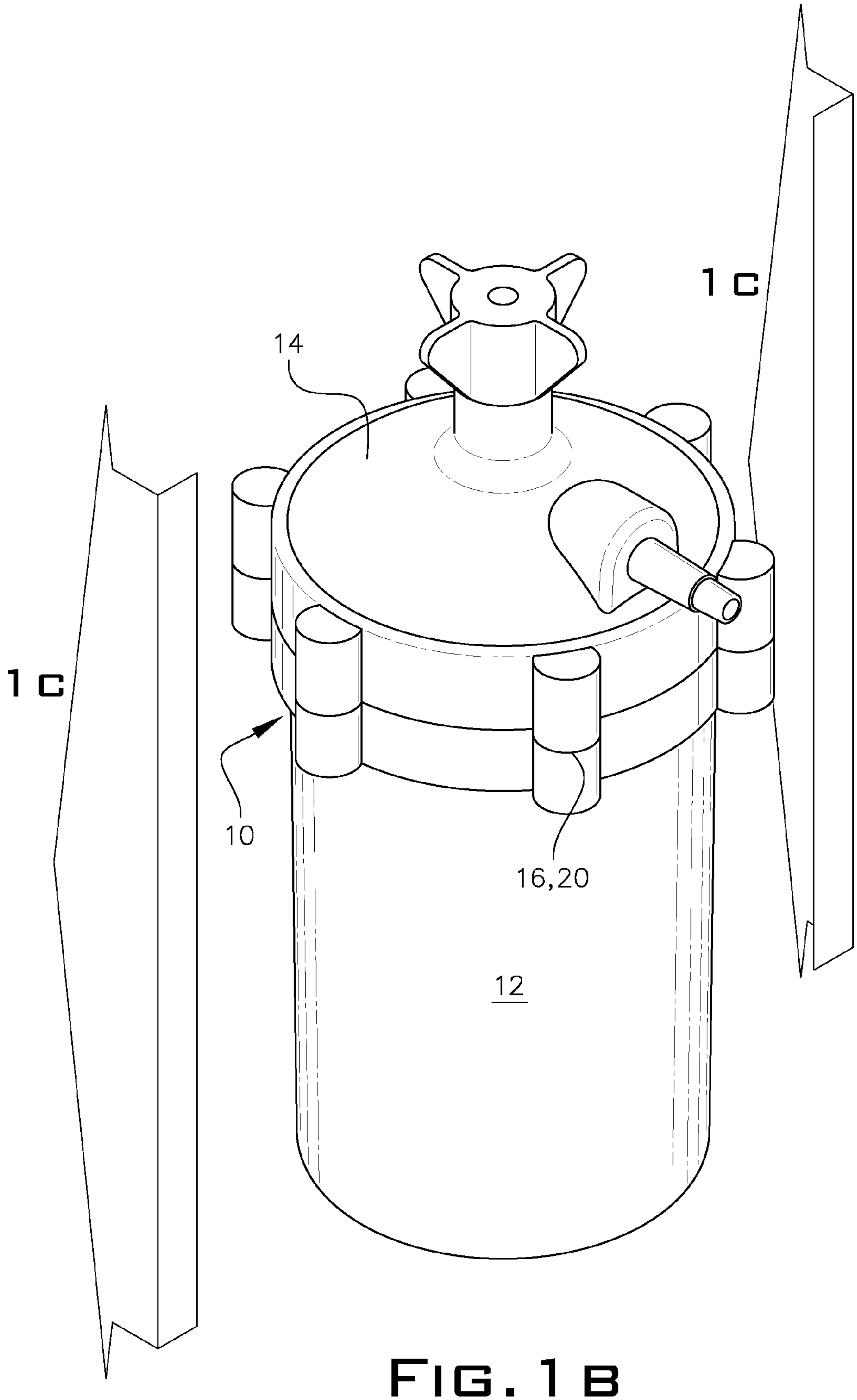
FIG. 1B is a perspective view of the embodiment of FIG. 1A depicting the upper and lower sections coupled.
Figure 1C:
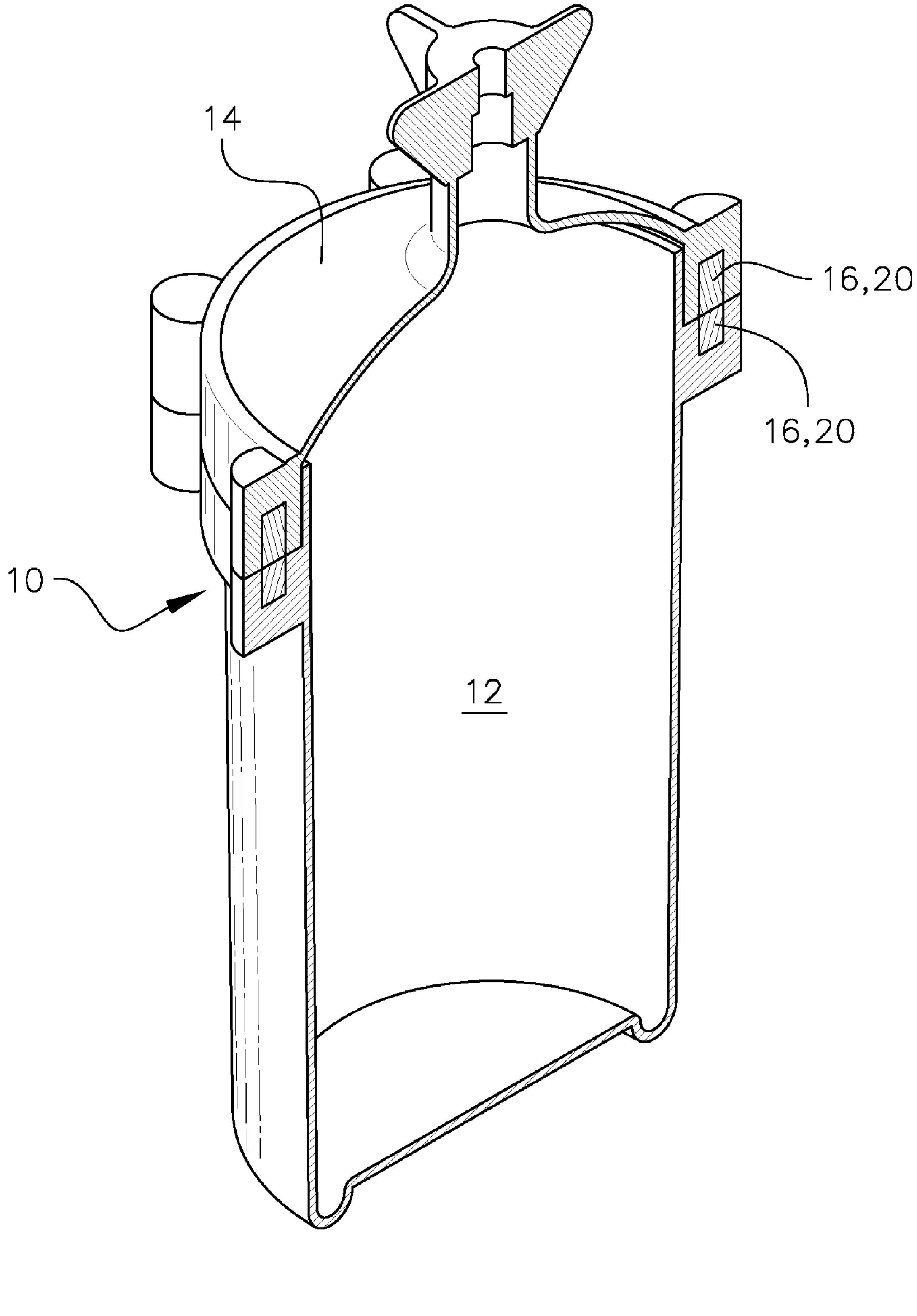
FIG. 1C is a cross-sectional view of the FIG. 1B.
Figure 2A:
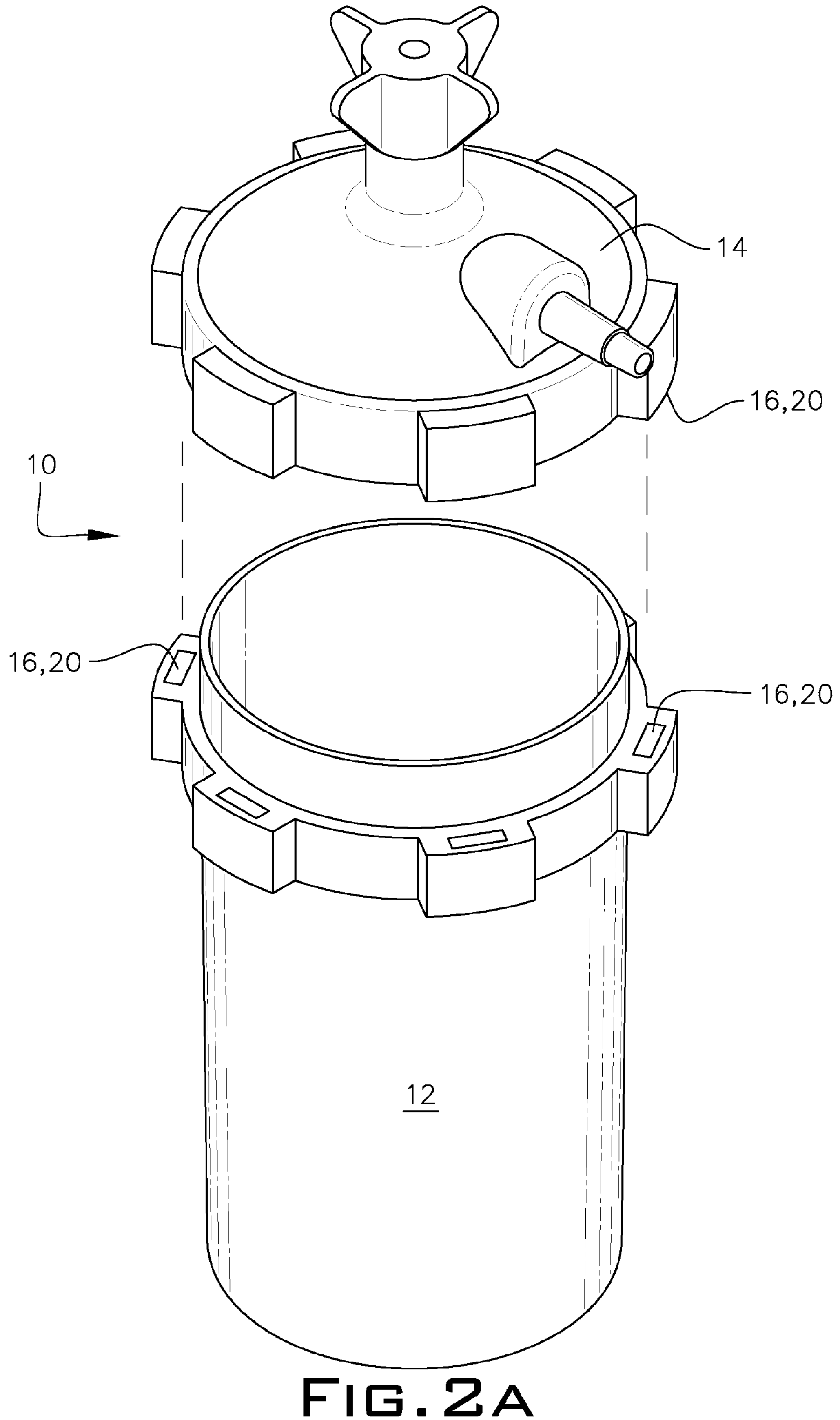
FIG. 2A is a perspective exploded view of another embodiment of the present invention depicting external generally rectangular or square magnets for the coupling of the upper and lower sections.
Figure 2B:
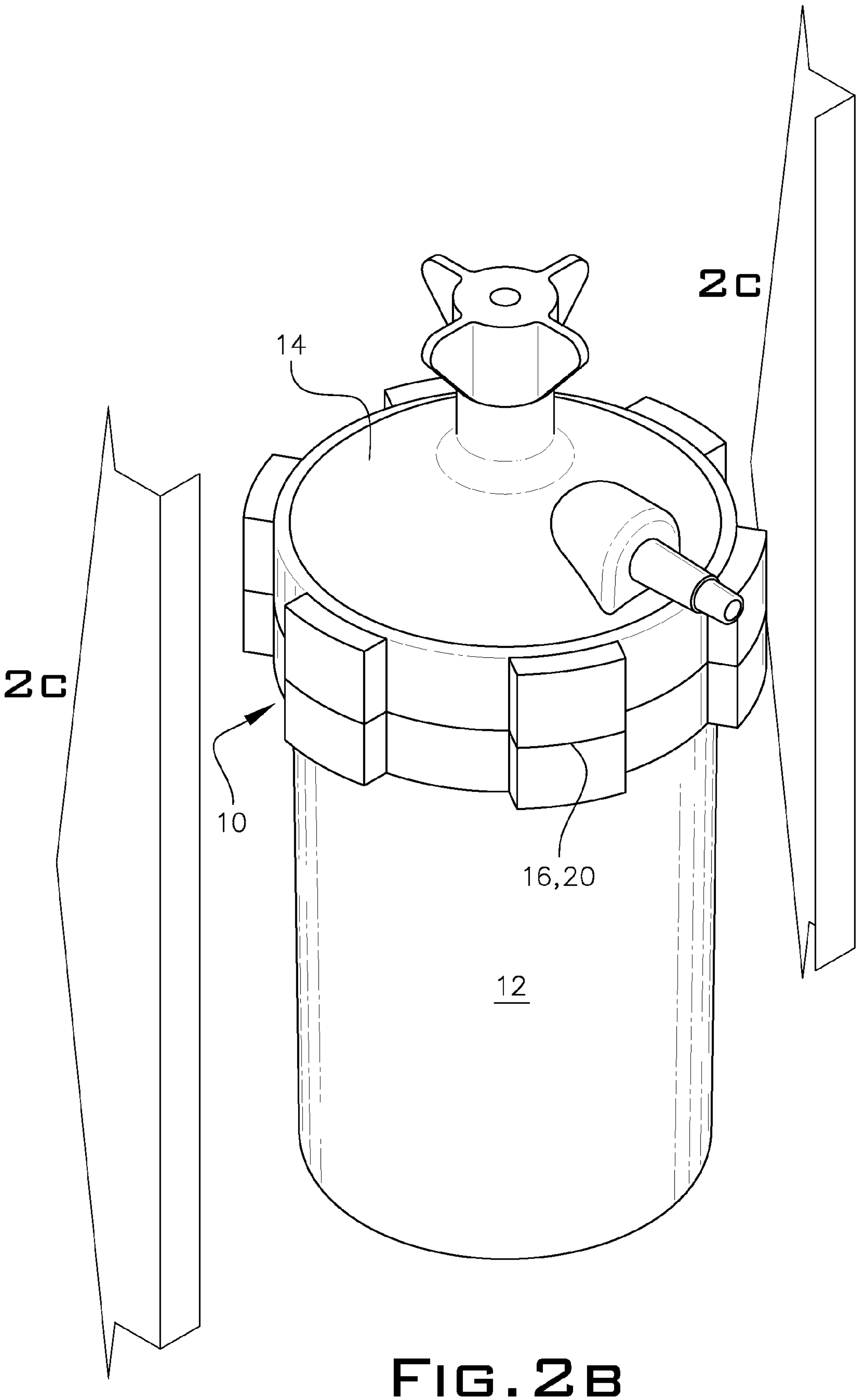
FIG. 2B is a perspective view of the embodiment of FIG. 2A depicting the upper and lower sections coupled.
Figure 2C:
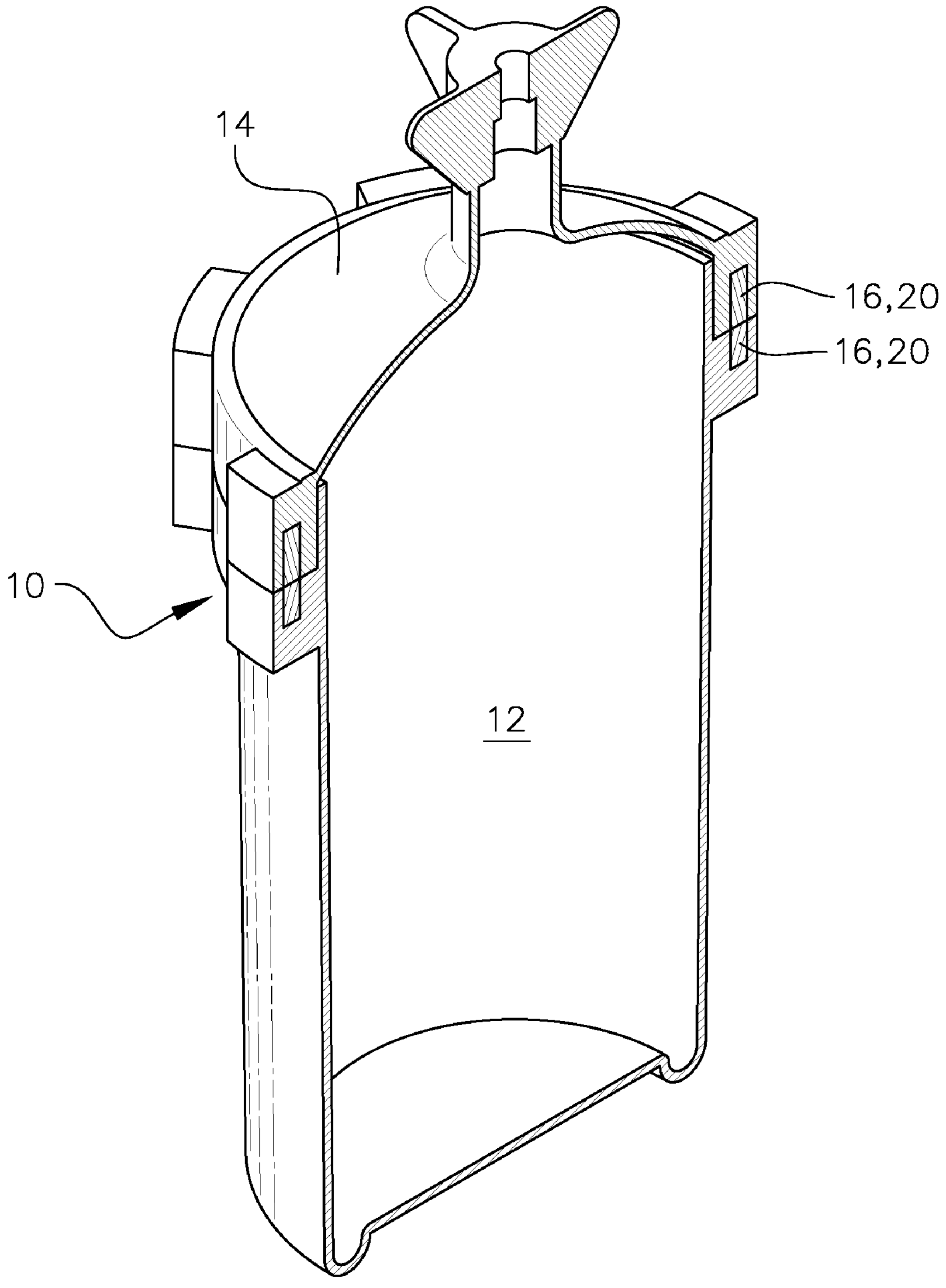
FIG. 2C is a cross-sectional view of the FIG. 2B.
Figure 3A:
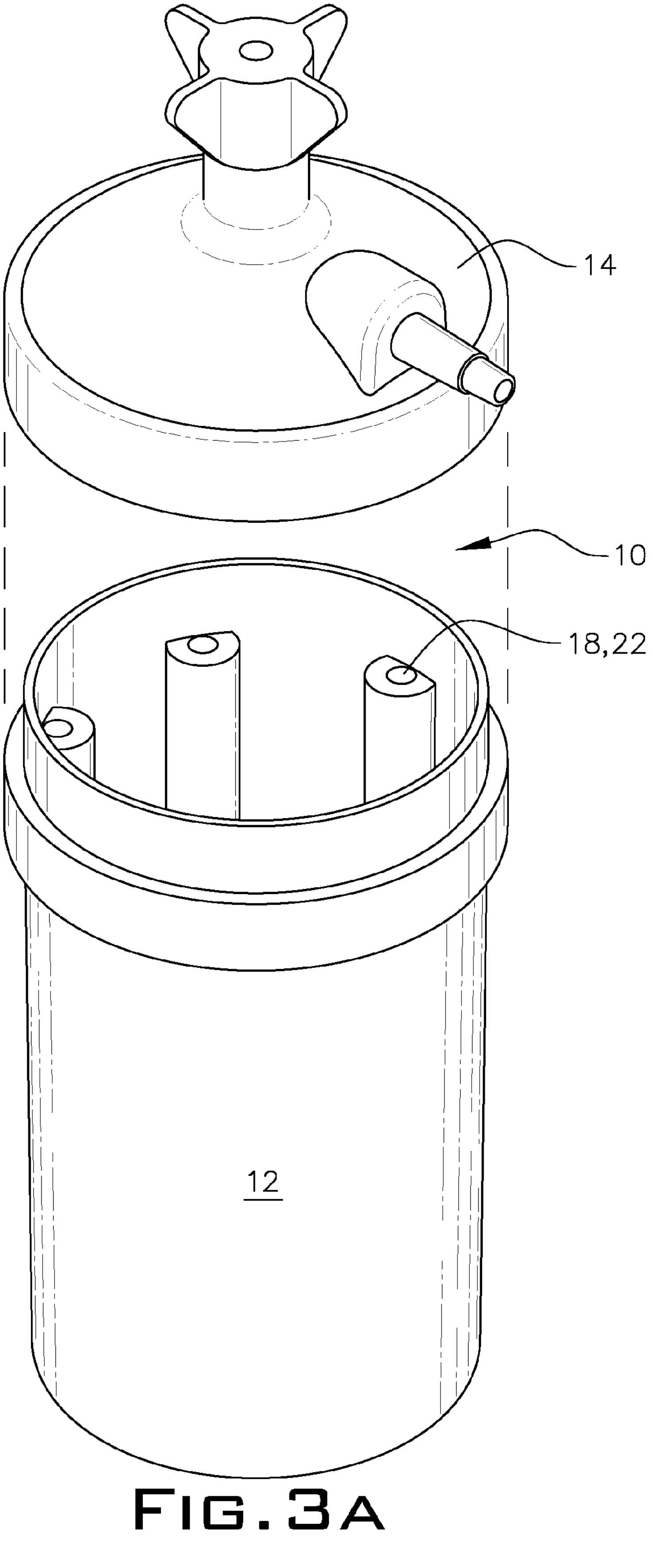
FIG. 3A is a perspective exploded view of still another embodiment of the present invention depicting internally generally round magnets for the coupling of the upper and lower sections.
Figure 3B:
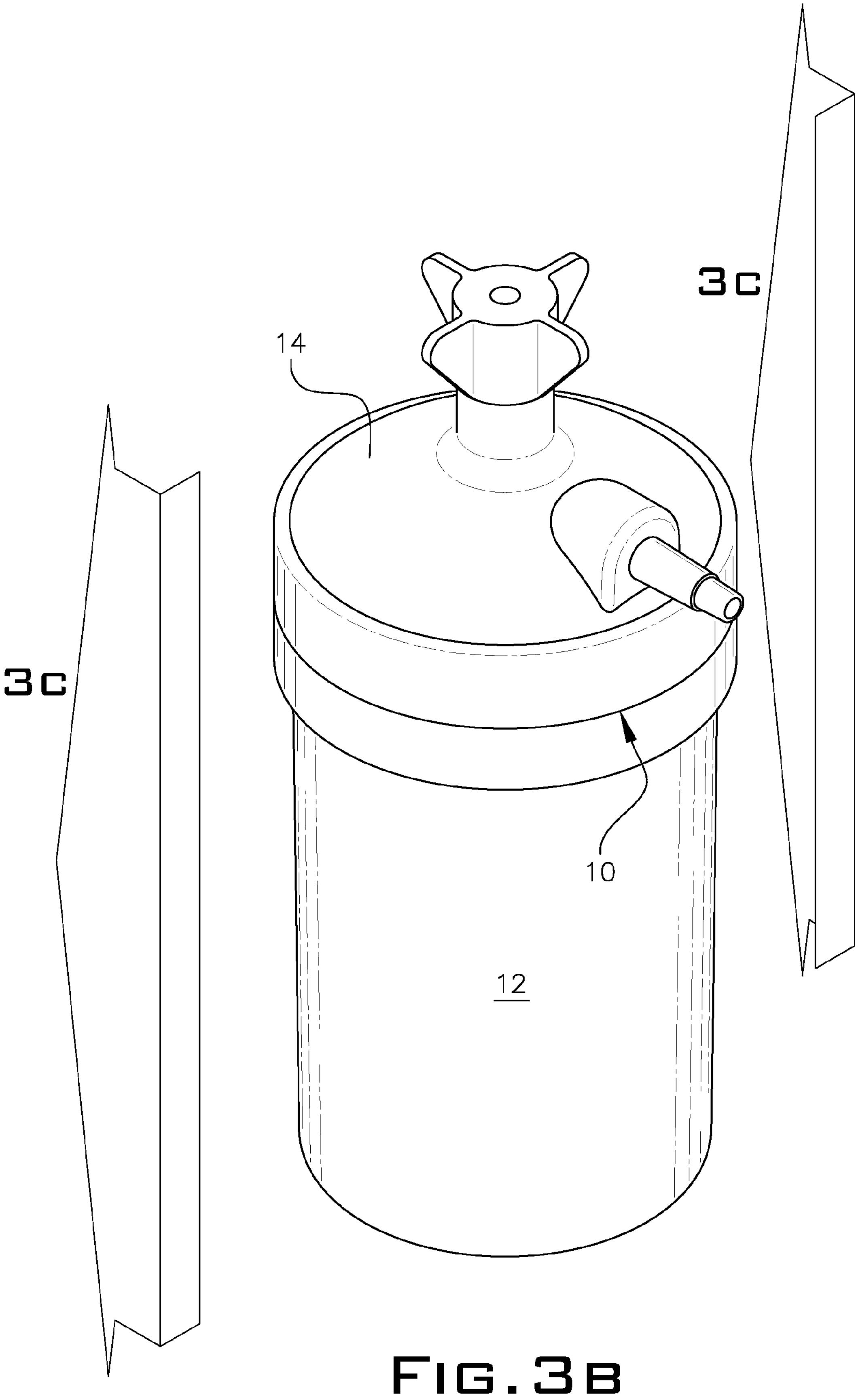
FIG. 3B is a perspective view of the embodiment of FIG. 3A depicting the upper and lower sections coupled.
Figure 3C:
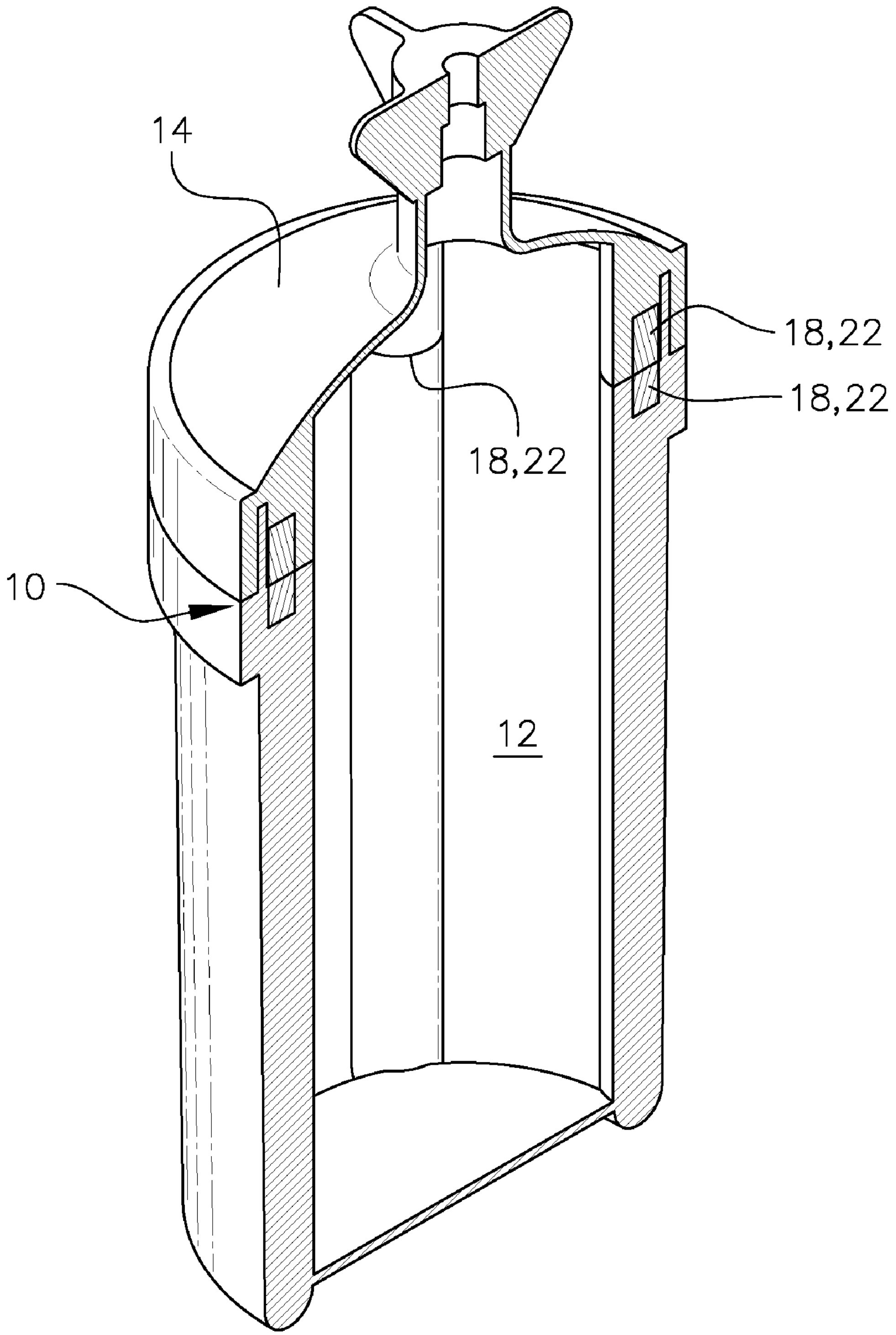
FIG. 3C is a cross-sectional view of the FIG. 3B.
Figure 4A:
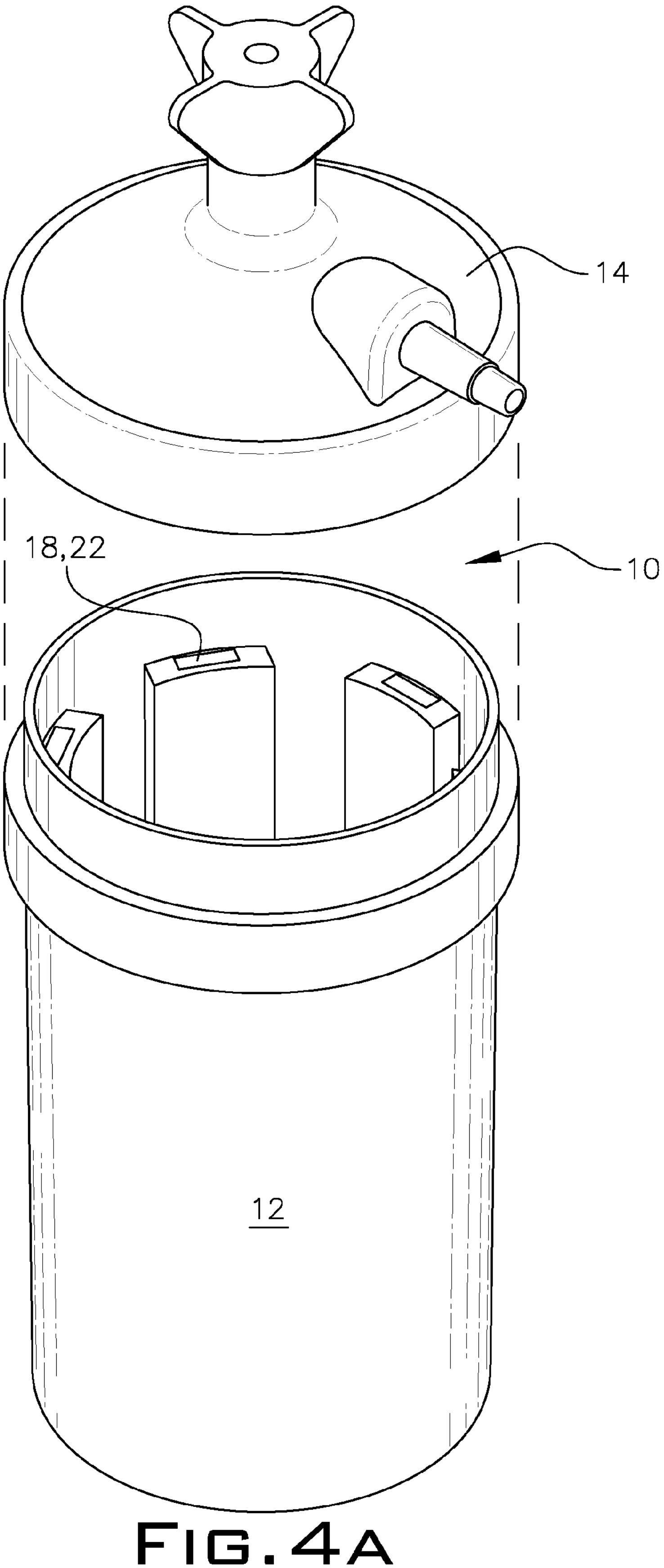
FIG. 4A is a perspective exploded view of still another embodiment depicting internally generally rectangular or square magnets for the coupling of the upper and lower sections.
Figure 4B:
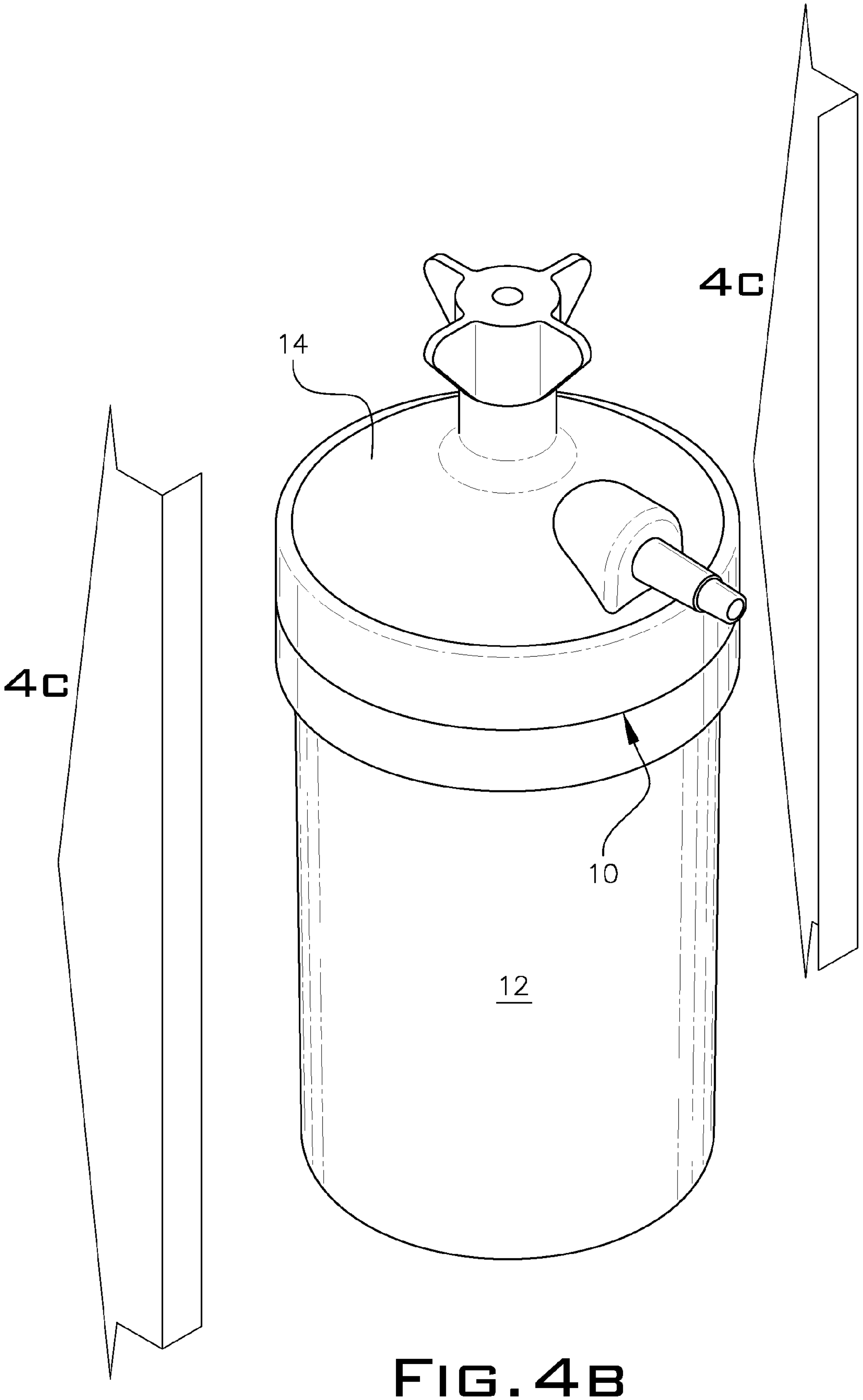
FIG. 4B is a perspective view of the embodiment of FIG. 4A depicting the upper and lower sections coupled.
Figure 4C:
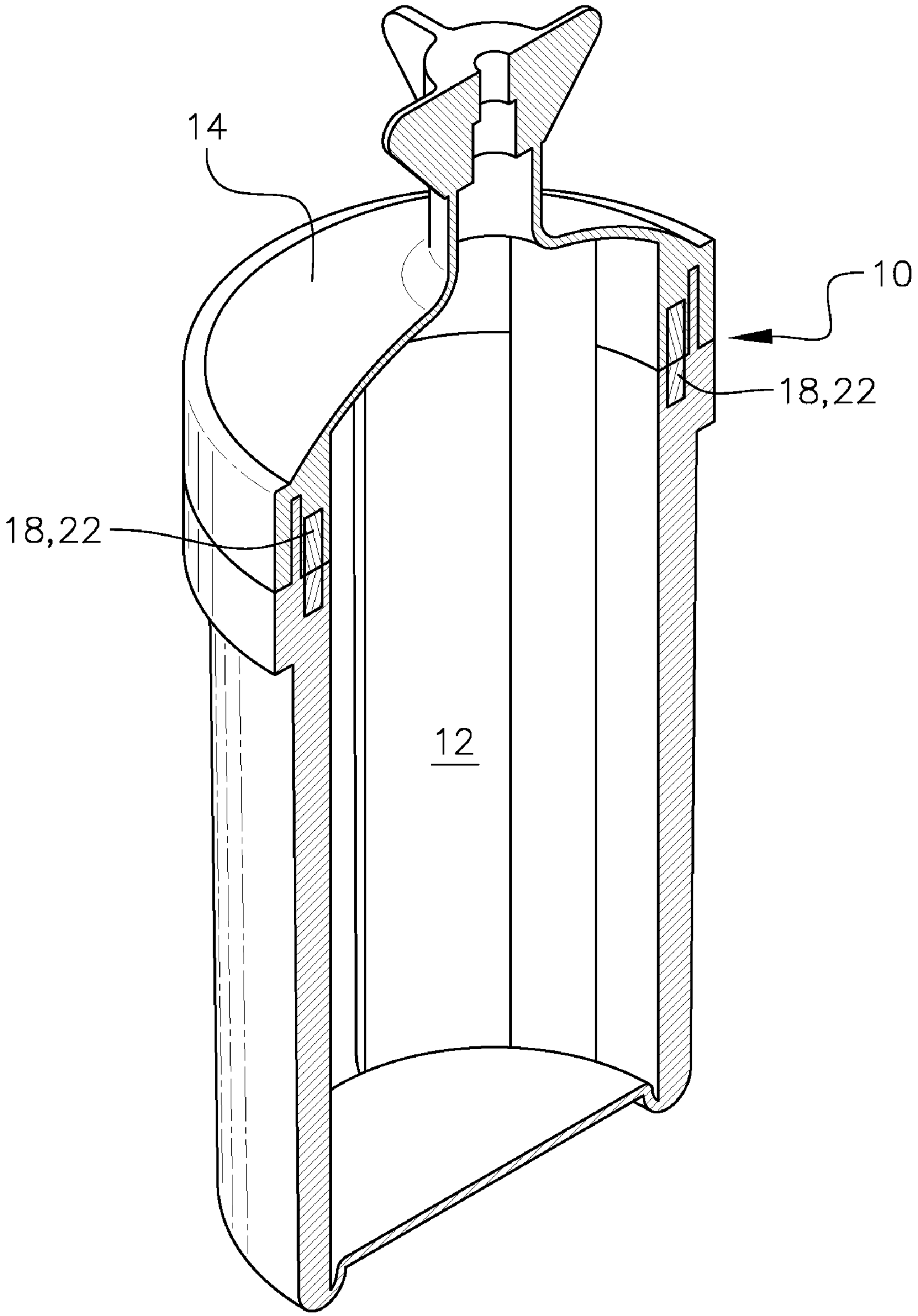
FIG. 4C is a cross-sectional view of the FIG. 4B.

Referring now to the drawings, various embodiments of the present invention are disclosed, which is a humidifier container used for humidifying a gas, such as oxygen, being utilized by a patient, and which has been specially modified with a magnetic coupling means for joining the cap and vessel of the container, the container in combination with the inventive coupling means being depicted generally as 10.

The present invention includes a humidifier container used for humidifying a gas, which is constructed with two primary components, a vessel or cup 12 and a cap or cover 14. This container 10 is modified or is provided with means 10 for coupling the cap 14 to the vessel 12 using magnetically attractive forces.

There are several configurations and embodiments contemplated for providing this feature.

Referring to FIGS. 1A-1C and 2A-2C, one configuration is a plurality of radially spaced-apart magnets 16 around an external perimeter of the cap 14 with a corresponding plurality of radially-spaced apart magnets 16 around an external perimeter of the vessel. In this embodiment, the plurality of radially spaced-apart magnets 16 around the external perimeter of the cap 14 are aligned with the corresponding plurality of radially-spaced apart magnets 16 around the external perimeter of the vessel 12 and configured so as to provide a secure engagement between the cap 14 and the vessel 12 during operation of the humidifying container.

In another embodiment, the means for coupling the cap 14 to the vessel 12 using magnetically attractive forces comprises a plurality of radially spaced-apart magnets 16 around an external perimeter of said cap 14 and a corresponding plurality of radially-spaced apart metal members 20 around an external perimeter of the vessel 12. The plurality of radially spaced-apart magnets 16 around the external perimeter of the cap 16 are aligned with the corresponding plurality of radially-spaced apart metal members 20 around the external perimeter of the vessel 12 and configured so as to provide a secure engagement between the cap 14 and the vessel 12 during operation of said humidifying container.

Alternatively, the magnets 16 may be on the vessel 12 side and the corresponding metal members 20 may be on the cap 14 side. In this embodiment, the humidifier container includes means for coupling the cap 14 to the vessel 12 using magnetically attractive forces configured with a plurality of radially spaced-apart metal members 20 around an external perimeter of the cap 14 and a corresponding plurality of radially-spaced apart magnets 16 around an external perimeter of the vessel 12. In this embodiment, the plurality of radially spaced-apart metal members 20 around the external perimeter of the cap 14 are aligned with the corresponding plurality of radially-spaced apart magnets 16 around the external perimeter of the vessel and configured so as to provide a secure engagement between the cap 14 and the vessel 12 during operation of said humidifying container.

Another variant is depicted in FIGS. 3A-3C and 4A-4C, where the means for coupling the cap 14 to the vessel 12 using magnetically attractive forces comprises a plurality of radially spaced-apart magnets 18 around an internal perimeter of the cap 14 and a corresponding plurality of radially-spaced apart magnets 18 around an internal perimeter of the vessel 12. In this embodiment, the plurality of radially spaced-apart magnets 18 around the internal perimeter of the cap 14 are aligned with the corresponding plurality of radially-spaced apart magnets 18 around the internal perimeter of the vessel 12 and configured so as to provide a secure engagement between the cap 14 and the vessel 12 during operation of said humidifying container.

Another variant for the humidifier container includes means for coupling the cap 14 to the vessel 12 using magnetically attractive forces configured with a plurality of radially spaced-apart metal members 22 around an internal perimeter of the cap 14 and a corresponding plurality of radially-spaced apart magnets 18 around an internal perimeter of the vessel 12. In this variant, the plurality of radially spaced-apart metal members 22 around the internal perimeter of the cap 12 are aligned with the corresponding plurality of radially-spaced apart magnets 18 around the internal perimeter of the vessel 12 and configured so as to provide a secure engagement between the cap 14 and the vessel 14 during operation of said humidifying container.

Another variant of the humidifier container 12 includes means for coupling the cap 14 to the vessel 12 using magnetically attractive forces comprising a plurality of radially spaced-apart magnets 18 around an internal perimeter of the cap 14 and a corresponding plurality of radially-spaced apart metal members 22 around an internal perimeter of the vessel 12. In this variant, the plurality of radially spaced-apart magnets 18 around the internal perimeter of the cap 14 are aligned with the corresponding plurality of radially-spaced apart metal members 22 around the internal perimeter of the vessel 12 and configured so as to provide a secure engagement between the cap 14 and the vessel 12 during operation of said humidifying container.

In the various embodiments discussed above, the humidifier container coupling means for the cap 14 to the vessel 12 using magnetically attractive forces can include various combinations of magnet 16,18 to magnet 16,18 coupling means or magnet 16,18 to metal member 20,22 coupling means. These magnets 16,18 and metal members 20,22 can be shaped as desired, however, it is contemplated that round-shaped magnets 16,18 or metal members 20,22 or rectangular-shaped magnets 16,18 or metal members 20,22 in cross-section are preferred.

Figure 5A:
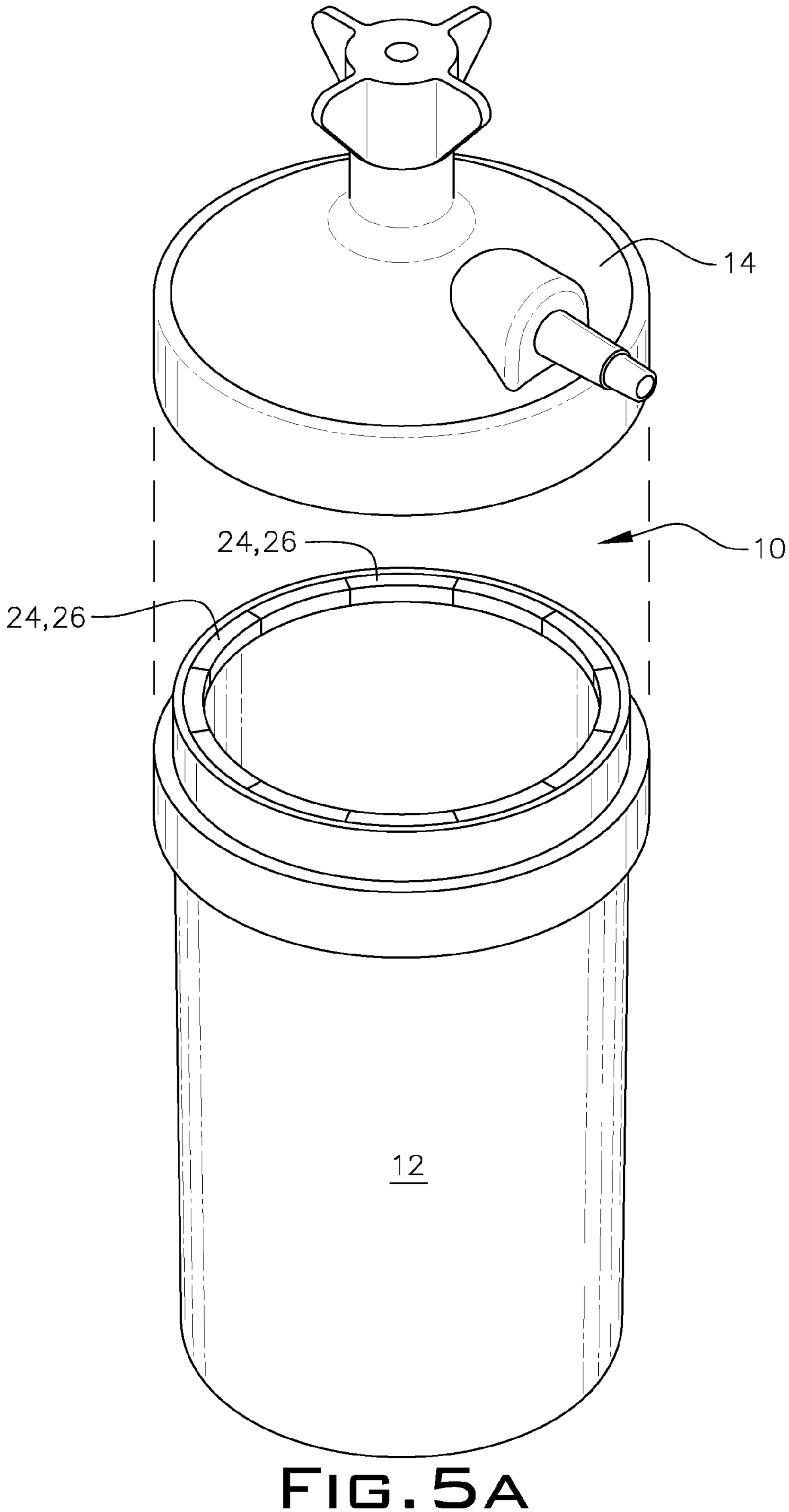
FIG. 5A is a perspective exploded view of still another embodiment using a ring or segmented ring of magnets for coupling the upper and lower sections.
Figure 5B:
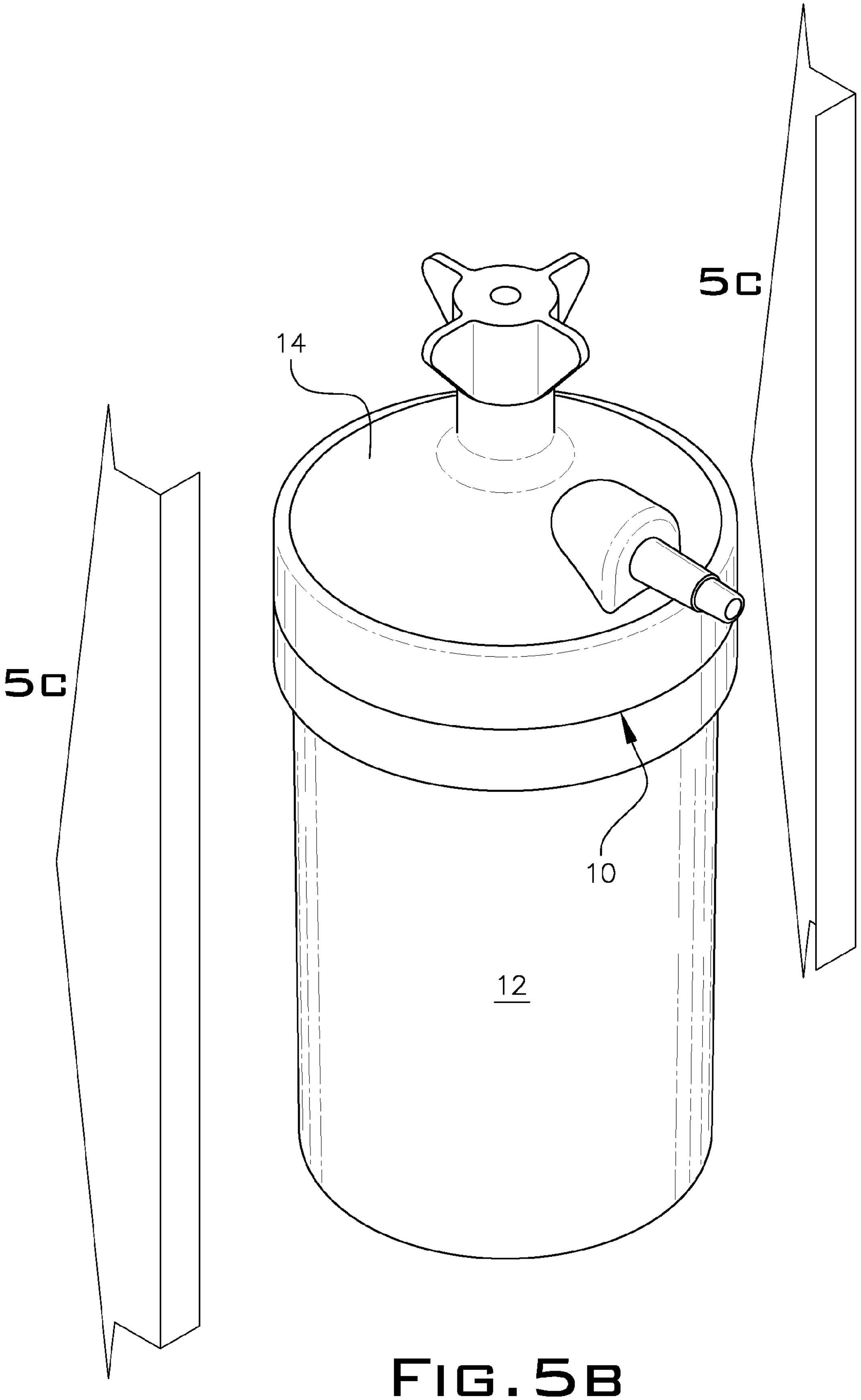
FIG. 5B is a perspective view of the embodiment of FIG. 5A depicting the upper and lower sections coupled.
Figure 5C:
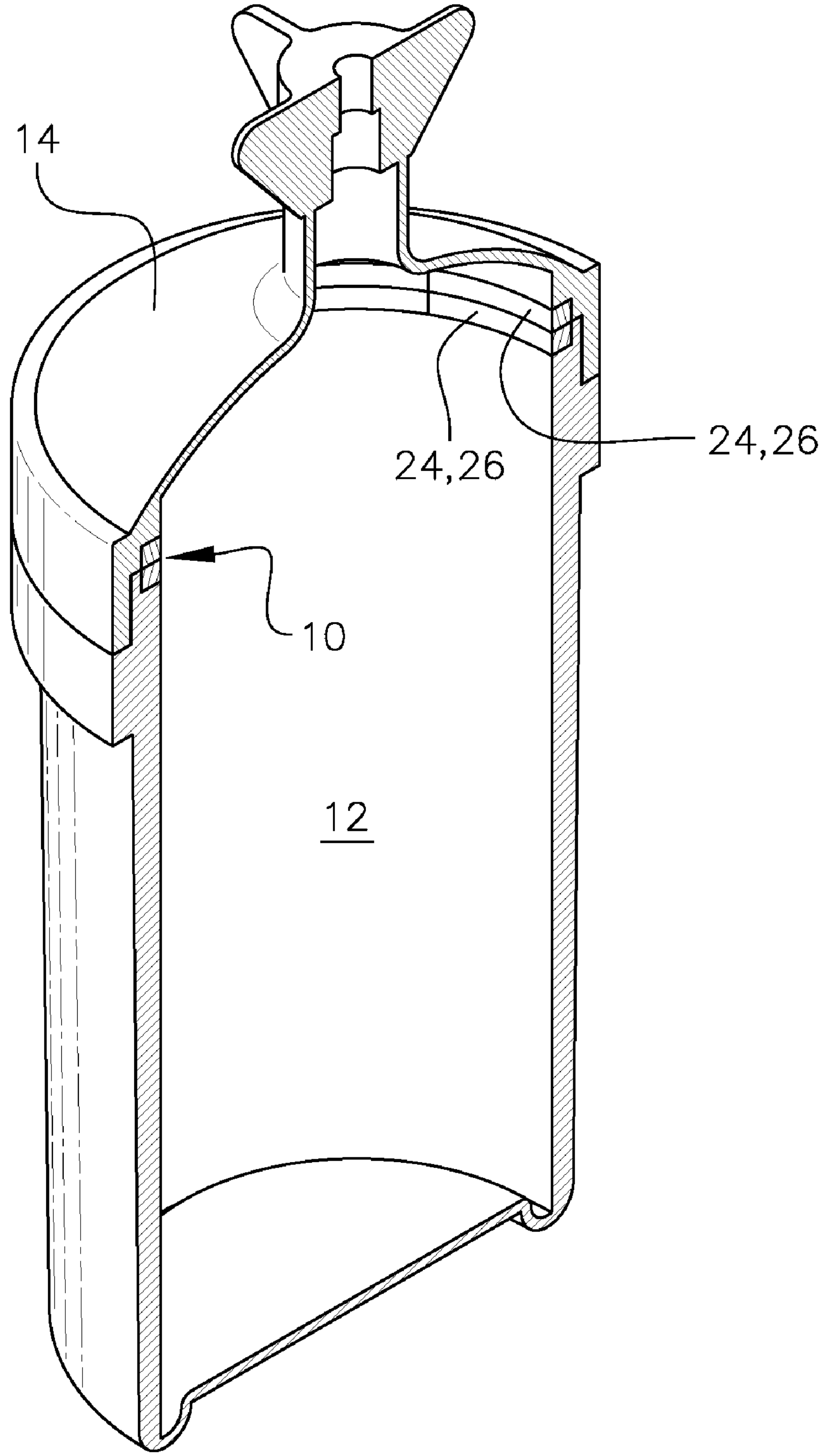
FIG. 5C is a cross-sectional view of the FIG. 5B.

FIGS. 5A-5C depict still another embodiment of the present invention using a ring or segmented ring of magnets 24 for coupling the upper and lower sections 14,12. As in the above embodiments, magnet 24 may instead be aligned with corresponding metal members 26. A solid ring may be molded within the respective upper and lower sections or segmented spaced-apart rings magnets/metal members 24,26 may be placed and configured to seal the upper and lower sections 14,12. Although not depicted, it is understood that an external ring or segmented ring configuration is contemplated as within the scope of the invention, although the preferred embodiment is one similar to that depicted in FIGS. 5A-5C.

It should be understood that the drawings, FIGS. 5A-5C, are conceptual only and the ring sections or segments depicted may preferably include unequal magnetic/non-magnetic sections, with the fastening sections slightly smaller and the spacing area slightly larger. The fastening sections would be slightly smaller allowing for a complete decoupling rotation position where as with equal sections there would always be some attraction between the sections as the surfaces are rotated about, attracting the coupling to the next fastening position. The ring assembly design also benefits from a thin vinyl (or other material) membrane (not shown) allowing for a better seal and uniform casting. In production, this will help to overcome any small abnormalities on the mating surfaces therein giving a uniform seal.

Figure 6A:
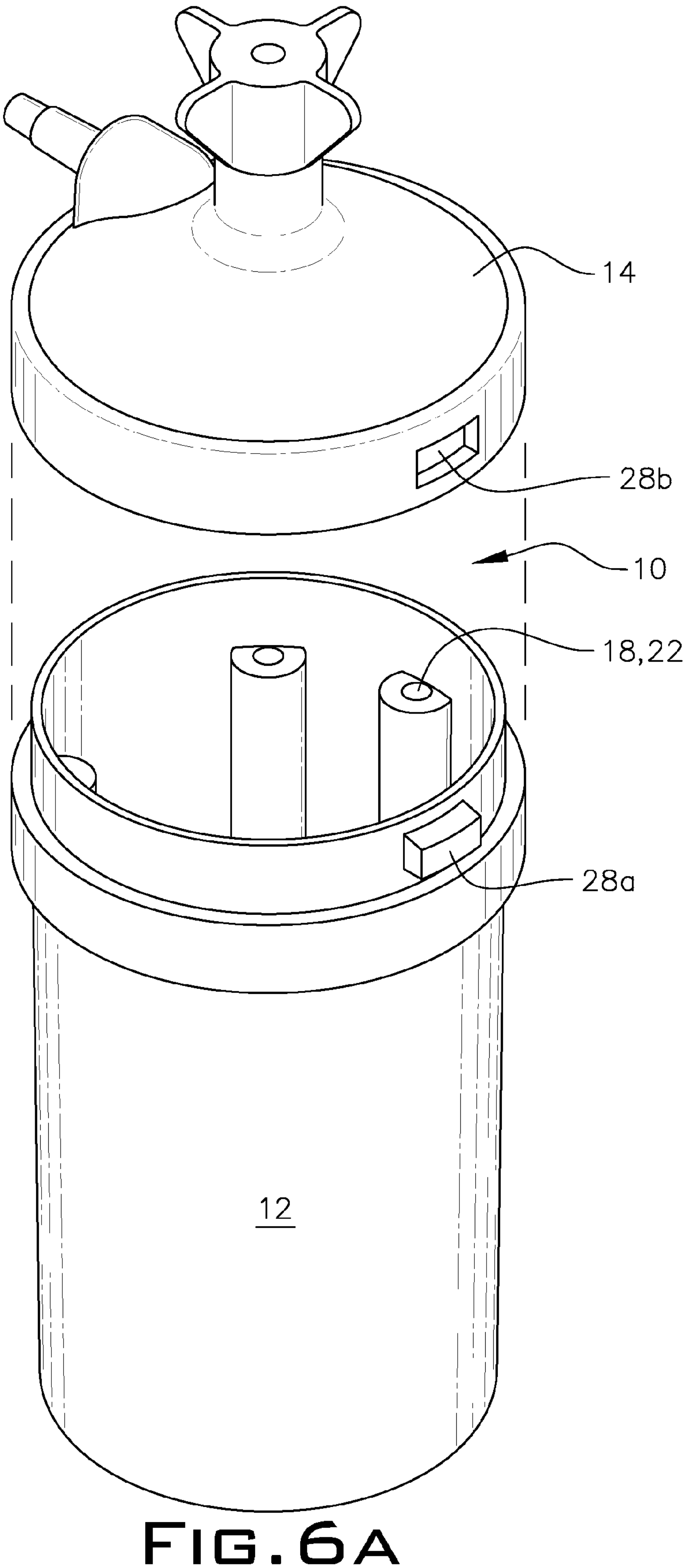
FIG. 6A is a perspective exploded view similar to the embodiment of FIG. 3A depicting an added locking tab and guide feature for facilitating the coupling of the upper and lower sections.
Figure 6B:
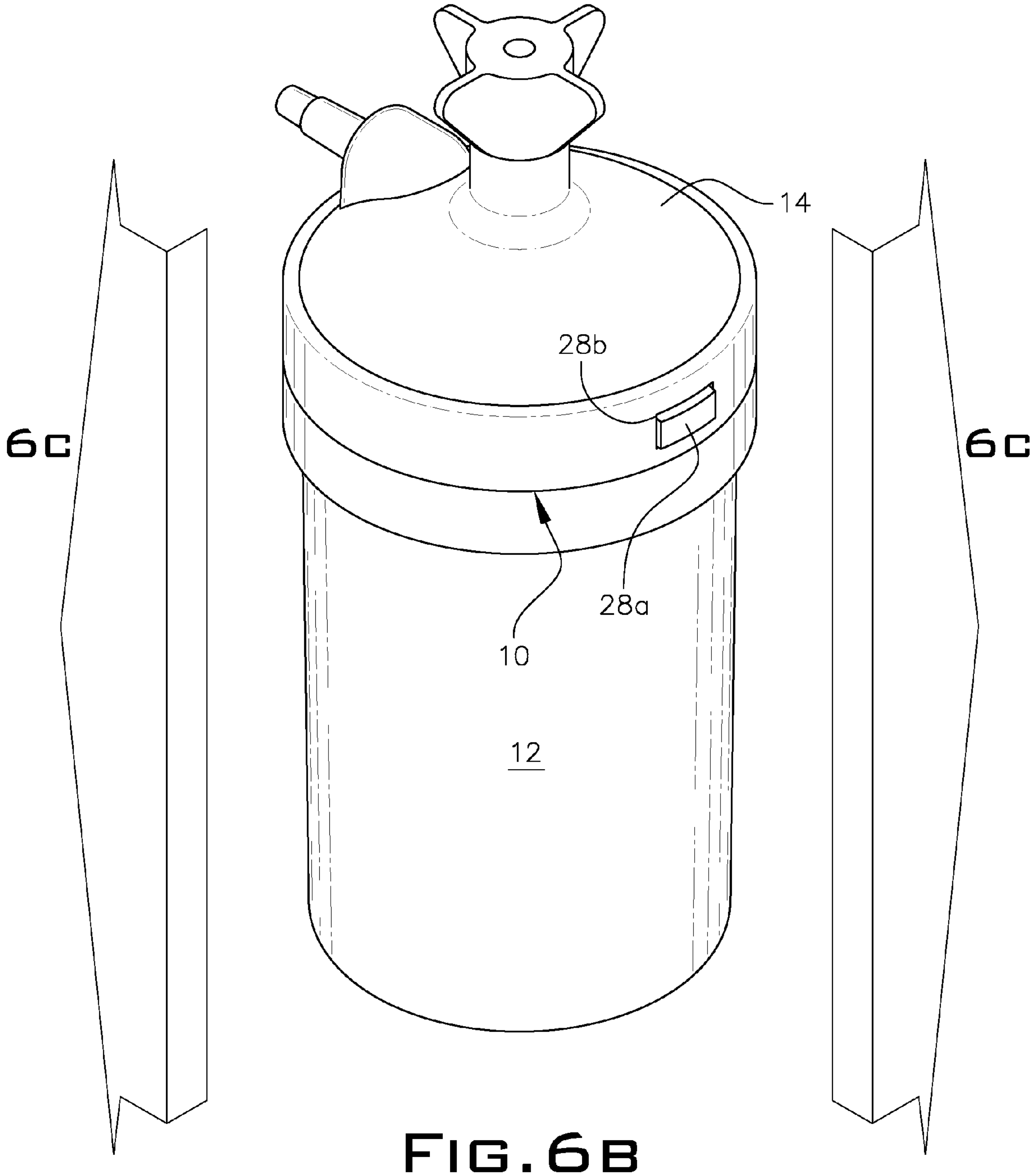
FIG. 6B is a perspective view of the embodiment of FIG. 6A depicting the upper and lower sections coupled.
Figure 6C:
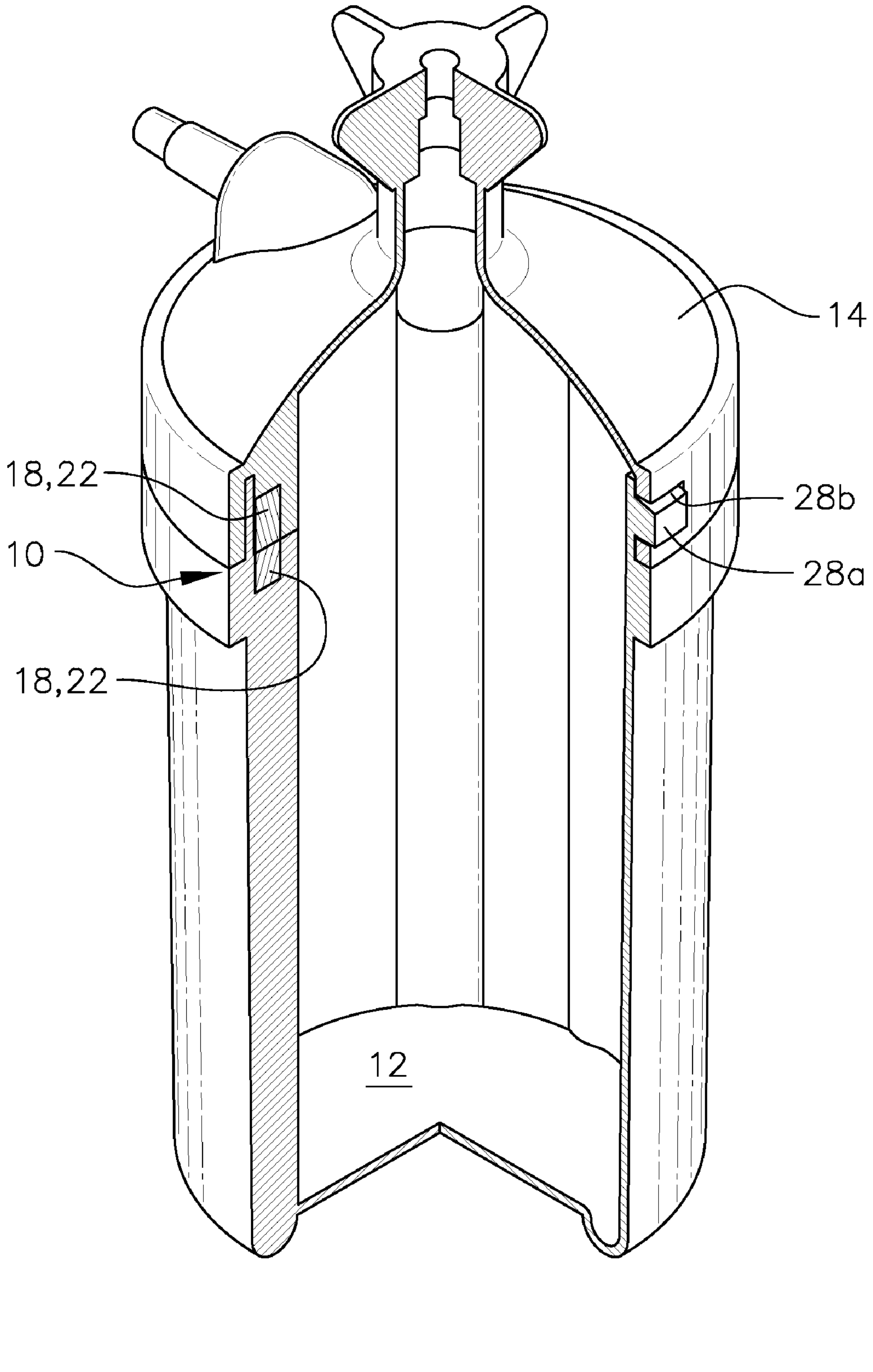
FIG. 6C is a cross-sectional view of the FIG. 6B.

FIGS. 6A-6C depict an added feature to facilitate the guiding and coupling of the upper and lower sections 14,12, no matter which configuration described above for magnetically coupling the container, using a tab 28*a* and slot 28*b* at a predetermined location around the perimeter of the coupling joint. Of course, it is understood that in the drawings, an example of having the slot 28*b* on the cover 14 side and mating tab 28*a* on the vessel 12 side is merely an example. The tab 28*a* may be located on the cover 14 side and the mating slot may be located on the vessel 12 side. This feature further serves as interlocking means for the cap 14 and vessel 12. The internal magnets depicted show one example of the use of the tab/slot feature. It is understood that this feature is applicable to any external magnet coupling configuration as well as any ring configuration depicted in the drawings and discussed in the written description above.

It should also be understood that although this specification describes a method of coupling a humidifier container using magnetic coupling means in lieu of a threaded means, the scope of the invention is intended to cover the use of magnetic coupling means in almost any circumstance where it would be beneficial to substitute a threaded connection with a magnetic coupling.

It should be understood that the preceding is merely a detailed description of one or more embodiments of this invention and that numerous changes to the disclosed embodiments can be made in accordance with the disclosure herein without departing from the spirit and scope of the invention. The preceding description, therefore, is not meant to limit the scope of the invention. Rather, the scope of the invention is to be determined only by the appended claims and their equivalents.

What is claimed is:

1. A method of coupling and securing a cap to a vessel of a humidifier container used for humidifying a gas, the method comprising:

providing a vessel and a cap, which comprises a humidifying container; and providing means for coupling said cap to said vessel using magnetically attractive forces, wherein said coupling means comprises a plurality of spaced-apart magnets around a perimeter of said cap or said vessel, and wherein said magnetically attractive forces of said coupling means are weakened for easier disassembly of said humidifier container when said cap or said vessel is turned relative to the other of said cap or said vessel.

2. The method according to claim 1, wherein said means for coupling said cap to said vessel using magnetically attractive forces comprises:

a plurality of radially spaced-apart magnets around an external perimeter of said cap; and a corresponding plurality of radially spaced-apart magnets around an external perimeter of said vessel, wherein said plurality of radially spaced-apart magnets around said external perimeter of said cap are aligned with said corresponding plurality of radially spaced-apart magnets around said external perimeter of said vessel and configured so as to provide a secure engagement between said cap and said vessel during operation of said humidifying container.

3. The method according to claim 1, wherein said means for coupling said cap to said vessel using magnetically attractive forces comprises:

a plurality of radially spaced-apart magnets around an external perimeter of said cap; and a corresponding plurality of radially spaced-apart metal members around an external perimeter of said vessel, wherein said plurality of radially spaced-apart magnets around said external perimeter of said cap are aligned with said corresponding plurality of radially spaced-apart metal members around said external perimeter of said vessel and configured so as to provide a secure engagement between said cap and said vessel during operation of said humidifying container.

4. The method according to claim 1, wherein said means for coupling said cap to said vessel using magnetically attractive forces comprises:

a plurality of radially spaced-apart magnets around an external perimeter of said vessel; and a corresponding plurality of radially spaced-apart metal members around an external perimeter of said cap, wherein said plurality of radially spaced-apart magnets around said external perimeter of said vessel are aligned with said corresponding plurality of radially spaced-apart metal members around said external perimeter of said cap and configured so as to provide a secure engagement between said cap and said vessel during operation of said humidifying container.

5. The method according to claim 1, wherein said means for coupling said cap to said vessel using magnetically attractive forces comprises:

a plurality of radially spaced-apart magnets around an internal perimeter of said cap; and a corresponding plurality of radially-spaced apart magnets around an internal perimeter of said vessel, wherein said plurality of radially spaced-apart magnets around said internal perimeter of said cap are aligned with said corresponding plurality of radially-spaced apart magnets around said internal perimeter of said vessel and configured so as to provide a secure engagement between said cap and said vessel during operation of said humidifying container.

6. The method according to claim 1, wherein said means for coupling said cap to said vessel using magnetically attractive forces comprises:

a plurality of radially spaced-apart metal members around an internal perimeter of said cap; and a corresponding plurality of radially-spaced apart magnets around an internal perimeter of said vessel, wherein said plurality of radially spaced-apart metal members around said internal perimeter of said cap are aligned with said corresponding plurality of radially-spaced apart magnets around said internal perimeter of said vessel and configured so as to provide a secure engagement between said cap and said vessel during operation of said humidifying container.

7. The method according to claim 1, wherein said means for coupling said cap to said vessel using magnetically attractive forces comprises:

a plurality of radially spaced-apart magnets around an internal perimeter of said cap; and a corresponding plurality of radially-spaced apart metal members around an internal perimeter of said vessel, wherein said plurality of radially spaced-apart magnets around said internal perimeter of said cap are aligned with said corresponding plurality of radially-spaced apart metal members around said internal perimeter of said vessel and configured so as to provide a secure engagement between said cap and said vessel during operation of said humidifying container.

8. The method according to claim 1, wherein said means for coupling said cap to said vessel using magnetically attractive forces comprises one of:

a mating internal magnetic ring or a plurality of mating spaced-apart magnetic segments forming said internal ring on each of said upper and lower sections of said humidifier container, and a mating internal magnetic ring or a plurality of mating spaced-apart magnetic segments forming said internal ring on one of said upper and lower sections of said humidifier container with a corresponding internal metal member ring or a plurality of corresponding mating metal member segments on the other of said upper and lower sections of said humidifier container.

9. The method according to claim 1, further comprising means for interlocking said cap to said vessel of said humidifier container, wherein said interlocking means comprises a mating tab and a slot, wherein said mating tab is configured to engage said slot when said cap and said vessel are magnetically coupled.

10. The method of claim 1, wherein pressure within said vessel and said cap is relieved when said pressure at least partially and at least transiently overcomes the magnetically attractive forces of said coupling means.

11. The method of claim 1, wherein said coupling means comprises four or more spaced-apart magnets around said perimeter of said cap or said vessel.

12. The method of claim 11, wherein said coupling means comprises six spaced-apart magnets around said perimeter of said cap or said vessel.

13. The method of claim 11, wherein said plurality of spaced-apart magnets are equally spaced around said perimeter of said cap or said vessel.

14. The method of claim 1, wherein said humidifier container holds water in said vessel and receives dry gas and dispenses humidified gas through said cap.

15. A humidifier container used for humidifying a gas comprising:

a cap;

a vessel; and means for coupling said cap to said vessel using magnetically attractive forces wherein said coupling means comprises a plurality of spaced-apart magnets around a perimeter of said cap or said vessel, and wherein said magnetically attractive forces of said coupling means are weakened for easier disassembly of said humidifier container when said cap or said vessel is turned relative to the other of said cap or said vessel.

16. The humidifier container according to claim 15, wherein said means for coupling said cap to said vessel using magnetically attractive forces comprises:

a plurality of radially spaced-apart magnets around an external perimeter of said cap; and a corresponding plurality of radially spaced-apart magnets around an external perimeter of said vessel, wherein said plurality of radially spaced-apart magnets around said external perimeter of said cap are aligned with said corresponding plurality of radially spaced-apart magnets around said external perimeter of said vessel and configured so as to provide a secure engagement between said cap and said vessel during operation of said humidifying container.

17. The humidifier container according to claim 15, wherein said means for coupling said cap to said vessel using magnetically attractive forces comprises:

a plurality of radially spaced-apart magnets round an external perimeter of said cap; and a corresponding plurality of radially spaced-apart metal members around an external perimeter of said vessel, wherein said plurality of radially spaced-apart magnets around said external perimeter of said cap are aligned with said corresponding plurality of radially spaced-apart metal members around said external perimeter of said vessel and configured so as to provide a secure engagement between said cap and said vessel during operation of said humidifying container.

18. The humidifier container according to claim 15, wherein said means for coupling said cap to said vessel using magnetically attractive forces comprises:

a plurality of radially spaced-apart magnets around an external perimeter of said vessel; and a corresponding plurality of radially spaced-apart metal members around an external perimeter of said cap, wherein said plurality of radially spaced-apart magnets around said external perimeter of said vessel are aligned with said corresponding plurality of radially spaced-apart metal members around said external perimeter of said cap and configured so as to provide a secure engagement between said cap and said vessel during operation of said humidifying container.

19. The humidifier container according to claim 15, wherein said means for coupling said cap to said vessel using magnetically attractive forces comprises:

a plurality of radially spaced-apart magnets round an internal perimeter of said cap; and a corresponding plurality of radially-spaced apart magnets round an internal perimeter of said vessel, wherein said plurality of radially spaced-apart magnets around said internal perimeter of said cap are aligned with said corresponding plurality of radially-spaced apart magnets around said internal perimeter of said vessel and configured so as to provide a secure engagement between said cap and said vessel during operation of said humidifying container.

20. The humidifier container according to claim 15, wherein said means for coupling said cap to said vessel using magnetically attractive forces comprises:

a plurality of radially spaced-apart metal members around an internal perimeter of said cap; and a corresponding plurality of radially-spaced apart magnets Mound an internal perimeter of said vessel, wherein said plurality of radially spaced-apart metal members round said internal perimeter of said cap are aligned with said corresponding plurality of radially-spaced apart magnets around said internal perimeter of said vessel and configured so as to provide a secure engagement between said cap and said vessel during operation of said humidifying container.

21. The humidifier container according to claim 15, wherein said means for coupling said cap to said vessel using magnetically attractive forces comprises:

a plurality of radially spaced-apart magnets round an internal perimeter of said cap; and a corresponding plurality of radially-spaced apart metal members around an internal perimeter of said vessel, wherein said plurality of radially spaced-apart magnets around said internal perimeter of said cap are aligned with said corresponding plurality of radially-spaced apart metal members around said internal perimeter of said vessel and configured so as to provide a secure engagement between said cap and said vessel during operation of said humidifying container.

22. The humidifier container according to claim 15, wherein said means for coupling said cap to said vessel using magnetically attractive forces comprises one of:

a mating internal magnetic ring or a plurality of mating spaced-apart magnetic segments forming said internal ring on each of said upper and lower sections of said humidifier container, and a mating internal magnetic ring or a plurality of mating spaced-apart magnetic segments forming said internal ring on one of said upper and lower sections of said humidifier container with a corresponding internal metal member ring or a plurality of corresponding mating metal member segments on the other of said upper and lower sections of said humidifier container.

23. The humidifier container according to claim 15, further comprising means for interlocking said cap to said vessel of said humidifier container, wherein said interlocking means comprises a mating tab and a slot, wherein said mating tab is configured to engage said slot when said cap and said vessel are magnetically coupled.

24. The humidifier container of claim 15, wherein pressure within said vessel and said cap is relieved when said pressure at least partially and at least transiently overcomes the magnetically attractive forces of said coupling means.

25. The humidifier container of claim 15, wherein said means for coupling said cap to said vessel comprises four or more spaced-apart magnets around said perimeter of said cap or said vessel.

26. The humidifier container of claim 25, wherein said means for coupling said cap to said vessel comprises six spaced-apart magnets around said perimeter of said cap or said vessel.

27. The humidifier container of claim 25, wherein said plurality of spaced-apart magnets are equally spaced around said perimeter of said cap or said vessel.

28. The humidifier container of claim 15, wherein said humidifier container holds water in said vessel and receives dry gas and dispenses humidified gas through said cap.

29. A humidifier container used for humidifying a gas comprising:

a cap;

a vessel; and means for coupling said cap to said vessel using magnetically attractive forces; wherein said means for coupling comprises: a plurality of spaced-apart magnets around a perimeter of said cap; and a corresponding plurality of spaced-apart magnets around a perimeter of said vessel, wherein said plurality of spaced-apart magnets around said perimeter of said cap are attracted to said corresponding plurality of spaced-apart magnets around said perimeter of said vessel and configured so as to provide a secure engagement between said cap and said vessel during operation of said humidifying container.

* * * * *